United States Patent [19]

Schmidt

[11] Patent Number: 4,562,270
[45] Date of Patent: Dec. 31, 1985

[54] PROCESS FOR PREPARING UNSATURATED SIX-MEMBERED LACTONES

[75] Inventor: Hans-Georg Schmidt, Niederkassel, Fed. Rep. of Germany

[73] Assignee: Dynamit Nobel AG, Troisdorf, Fed. Rep. of Germany

[21] Appl. No.: 540,731

[22] Filed: Oct. 11, 1983

Related U.S. Application Data

[60] Continuation-in-part of Ser. No. 282,689, Jul. 13, 1981, Pat. No. 4,424,369, which is a division of Ser. No. 218,593, Dec. 19, 1980, Pat. No. 4,348,535.

[30] Foreign Application Priority Data

Dec. 22, 1979 [DE] Fed. Rep. of Germany ....... 2952068
Dec. 3, 1980 [DE] Fed. Rep. of Germany ....... 3045455
Dec. 6, 1980 [DE] Fed. Rep. of Germany ....... 3046059
Jul. 15, 1983 [DE] Fed. Rep. of Germany ....... 3325505

[51] Int. Cl.$^4$ .......................................... C07D 309/32
[52] U.S. Cl. .................................................... 549/294
[58] Field of Search ......................................... 549/294

[56] References Cited

U.S. PATENT DOCUMENTS 4,235,780 11/1980 Kondo et al. ...................... 549/273
4,237,058 12/1980 Kondo et al. ...................... 549/273

OTHER PUBLICATIONS

Aumann et al., Chem. Abs. 92:111134r.

*Primary Examiner*—Jane T. Fan
*Attorney, Agent, or Firm*—Sprung Horn Kramer & Woods

[57] ABSTRACT

There are disclosed and claimed substituted cyclic lactones and process for preparation thereof. In particular, there are disclosed substituted cyclic lactones having alkyl substituents on the ring, especially such lactones having substituents on the ring of which two on the same carbon atom.

Additionally, the invention herein disclosed and claimed relates to a process for the preparation of lactones by heating a six-membered hydroxy substituted lactone in the presence of a catalyst.

17 Claims, No Drawings

PROCESS FOR PREPARING UNSATURATED SIX-MEMBERED LACTONES

CROSS-REFERENCE TO RELATED APPLICATION

This is a continuation in-part of co-pending application Ser. No. 282,689 filed July 13, 1981, now U.S. Pat. No. 4,424,369, issued Jan. 3, 1984, which in turn is a divisional application of Ser. No. 218,593, filed Dec. 19, 1980 now U.S. Pat. No. 4,348,535, the disclosures of which are hereby incorporated herewith by reference. This application is also related to U.S. patent application Ser. No. 625,753, filed June 28, 1984, now pending, and U.S. patent application Ser. No. 375,060, filed May 5, 1982, now U.S. Pat. No. 4,509,914, issued Apr. 2, 1985.

BACKGROUND OF THE INVENTION

Field of the Invention

This invention is directed to the preparation of certain substituted cyclic lactones having a degree of unsaturation in the ring. In particular, this invention is directed to the preparation of substituted cyclic lactones having alkyl substituents on the ring, especially substituted lactones wherein there are two alkyl substituents on the ring, which are on the same carbon atom.

More specially, this invention relates to a process for the preparation of such substituted lactones and other lactones by heating a hydroxy substituted lactone in the presence of a catalyst.

SUMMARY OF THE INVENTION

Broadly, this invention contemplates a process for the preparation of a lactone of the formula

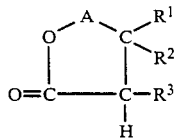

wherein A is a —CH=CH-moiety, $R^1$, $R^2$ and $R^3$ are hydrogen or $C_1$ to $C_{10}$ alkyl which comprises heating a lactone of the formula

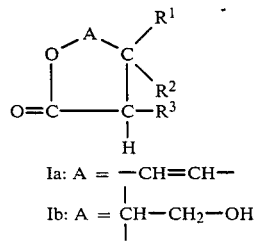

Ia: A = —CH=CH—
Ib: A = CH—CH$_2$—OH wherein A is a

—CHCH$_2$OH group and $R^1$, $R^2$ and $R^3$ have the meaning given above at a temperature ranging from 200° to 500° C. in the presence of a catalyst. The reaction takes place with or without a catalyst. In the presence of a catalyst the reaction rate is improved.

Numerous catalysts have been discovered as useful for the preparation of a lactone in accordance with the invention.

Catalyst which are useful in accordance with the invention, include:

(a) the oxides of a wide range of metals including aluminum, silicon, chromium, iron, gallium, tungsten, molybdenum, thorium, zinc, titanium, zirconium, nickel, manganese and the rare earth metals. Mixed oxides of these elements are also useful. Those metals capable of more than one oxide form, e.g. iron, can be used in any of the oxide forms e.g. ferric oxide, ferric oxide, etc.;

(b) alumino silicates including both amorphous alumino silicates and crystalline alumino silicates including both zeolitic and non-zeolitic alumino silicates. Included within this class are non-zeolitic alumino silicates such as clay e.g. montmorillonite and kaolin.

Zeolitic crystalline alumino silicates which are contemplated include both natural and synthetic zeolites including zeolites X, Y, T, A, faujasite, chaubasite, mordenite, erionite, offretite, ZSM-5, ZKY, ZK22, Beta etc. These materials can be in their natural form or in an ion exchanged form. They can be in the hydrogen form, ammonium form, decationized form, rare earth exchanged form or an exchange from wherein alkali or alkaline earth metals have been exchanged for other metal values such as calcium, magnesium, zinc, or any of the metals of paragraph (a). Preferably, they are in a form in which the alkali metal content is less than 4% by-weight.

(c) alkalin and alkaline earth metal salts of sulfur and phosphoric acid. Included within this group are sodium sulphate, sodium bisulphate, $K_2HPO_4$, $KH_2PO_4$. Aromatic acids contemplated include in particular benzoic and toluic acids. Phthalic acids are also contemplated as well as any of the following aromatic acids: toluene sulfonic acids.

(d) Bronsted and Lewis acids including, in particular, HF, HCl, boron-trifluoride, phosphoric acid, boron tri-etherate, aluminum tri-chloride, zinc chloride, sulfuric acid, ferric chloride, $AlBr_3$, $PCl_3$ and $PCl_5$ (e) Anhydrides of organic or inorganic acids. Included within the term "anhydrides of inorganic acids" is, for example, $P_2O_5$.

Particularly contemplated anhydrides of organic acids are those corresponding to the formula

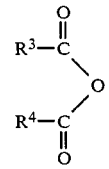

wherein each $R^3$ and $R^4$ is independently a substituted or unsubstituted, saturated or unsaturated aliphatic radical up to 18 carbon atoms, preferably up to 12 carbon atoms, an aryl radical of up to 18 polycyclic carbon atoms, preferably up to 12 carbocyclic carbon atoms where the rings can be substituted or unsubstituted, saturated or unsaturated; a substituted or unsubstituted cyclo-aliphatic radical with 3 to 18 carbon atoms in the ring.

(f) Esters of inorganic acid including in particular esters of alkyl or aromatic moieties of 1 to 10 carbon atoms. Particularly contemplated esters of inorganic acids include: trimethylphosphate and tricresylphosphate, (g) Sheet silicates including: saponite, beidellite, hectorite, flurohectorite, vermiculite, pyrophyllite, talc, muscovite, phlogepite, kaolinite, illite, chlorite.

Generally speaking, the catalyst can be employed in a supported or unsupported form and in any event the active component is present in the reaction mixture in an amount of between less than 100 weight percent, preferably less than 50 weight percent, based upon the weight of the reaction mixture.

The process can be carried out with or without the use of a solvent. When a solvent is employed, it is preferred to utilize a hydrocarbon or chlorinated hydrocarbon solvent. The solvents can be chlorinated or unchlorinated aliphatic or aromatic hydrocarbons, in particular, cyclohexane, Decalin, toluene and xylene. Phosphoric acid esters such as tri-cresyl phosphate are especially useful.

Generally speaking, in carrying out the process one heats the reaction vessel including the catalyst and stirs the vessel until the hydroxy lactone is converted to the dihydro-α-pyrone. For instance, one can heat the catalyst in a stirring vessel and add 5-hydroxymethyl furanone thereto and continuously remove the resultant reaction product (water + the desired compounds) by the use of a distillation column. It is however, unnecessary to remove the products of the reaction. Instead, the furanone reactant can be trickled through a tube maintained at the desired reaction temperature and containing therewithin the catalyst to be employed. The reaction mixture can then be collected in a cooled receiver from which the corresponding pyrone can be obtained.

The process of the invention can be carried out using a supported or unsupported catalyst. When the catalyst is a supported catalyst it can be supported by an active or inert substrate. One can use for instance a zeolite or clay supported on an amorphous $Al_2O_3/SiO_2$ substrate or carrier. Alternatively one can use glass beads as the carrier, or one can use silica, zirconia, titania, etc. Activated carbon is also a suitable carrier for use in the process.

The catalyst can be in the form of extrudates or spheres or can be used in powder form or moulding shapes.

When compounds are reacted in accordance with the present invention, in a process wherein a metal oxide or silicate material is not used as the catalyst it is preferable to carry out the process in a stirring vessel with the furanone reactant heated to the requisite temperature with or without the co-presence of a solvent and a continuously distill off the reaction products. The process is carried out at reduced or elevated pressures but preferably is conducted at atmospheric pressure.

The process of the invention is especially useful in preparing a lactone of the formula

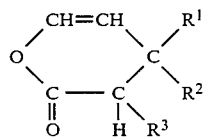

wherein all of the radicals $R^1$, $R^2$ and $R^3$ are alkyl radicals. Preferably these radicals are $C_1$ to $C_8$ alkyl radicals. Preferably they are the same as one another and are selected from the group consisting of methyl, ethyl, propyl and butyl.

The process can also be employed to prepare a substituted lactone of the formula

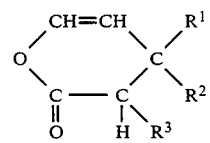

wherein only one of the $R^1$, $R^2$ and $R^3$ radicals is alkyl. It is preferred that $R^1$ be the alkyl radical although either $R^2$ or $R^3$ can be the alkyl radical. In any event it is preferred that the alkyl radical have 1 to 8 carbon atoms and it is particularly preferred that it be selected from the group consisting of methyl, ethyl, propyl or butyl e.g. n-butyl.

The process of the invention can also be carried out to prepare a lactone of the formula

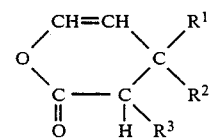

wherein $R^1$, $R^2$ and $R^3$ are independently hydrogen and $C_1$ to $C_{10}$ alkyl, especially $R^1=R^2=CH_3$, $R^3=H$.

Lactones Ia produced by the process of the invention are useful intermediates in the manufacture of plant protected agents, pharmaceuticals and dyes. They can be converted into lactones of the formula V and to the ester VI

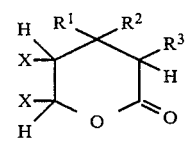

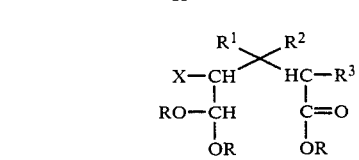

whereby each R moiety is independently an alkyl group of 1 to 4 carbon atoms and each $R^1$, $R^2$ and $R^3$ is independently hydrogen or is $C_1$ to $C_{10}$ alkyl group an X is chlorine or bromine by contacting lactones Ia produced in accordance with the process discussed supra in an inert reaction mixture with chlorine or bromine. Preferably the reaction is conducted at a temperature between $-10°$ and $+40°$ C. The chlorine or bromine is employed in a stoichiometric amount but can be employed in an excess. Solvents can be utilized for the conversion including liquid chlorinated hydrocarbons, liquid hydrocarbons and ethers e.g. carbon tetrachloride, pentane, diethyl ether. The ester form VI is obtained by reacting the halogen substituted lactone V with an alkali or alkaline earth-metal alcoholate in the presence of a superstoichiometric amount of an aliphatic alcohol e.g. alkanol with 1 to 10 carbon atoms. It is preferred that the alcoholate be an alkali metal alcoholate especially sodium alcoholate e.g. sodium methylate and that the amount of alcohol be present in a 2 to 200 fold molar excess. The process is conducted at a temperature between +10° and +60° C. and the esters obtained by this reaction are isolated by fractional distillation. If no excess alcoholate is present, this distillation can be carried out directly subsequent to the reaction. In the presence of excess alcoholates it is, however, preferable to remove these by extraction with water and to subsequently separate the raw product by distillation.

There is further contemplated the preparation of an acetal of 2,2-dialkyl-3-formyl-cyclopropane carboxylic acid alkyl ester of the formula

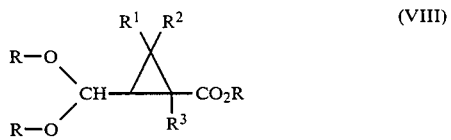
(VIII)

from the substituted carboxylic acid ester of formula VI above. In formula (VIII) above, each R moiety is independently an alkyl group of 1 to 4 carbon atoms and each $R^1$, $R^2$ and $R^3$ group is independently hydrogen or an alkyl group of 1 to 10 carbon atoms. The same is prepared by contacting a lactone of formula IV=Ia supra with bromine or chlorine to obtain the corresponding dihalide of formula V. The dihalide is thereafter reacted with an alcoholate of formula (VII) in the presence of an alkanol of formula (VIIa) supra whereby to form the corresponding ester whose formula is

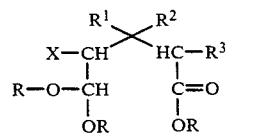
VI wherein each R group is independently an alkyl radical of 1 to 4 carbon atoms. The acetal of 2,2-dialkyl-3-formyl-cyclo-propane carboxylic acid alkyl ester is in turn prepared by reacting the ester prepared from the dihalo lactone with an alcoholate of the formula (VII) above whereby cyclization occurs and the cyclopropane carboxylic acid structure of formula (VIII) supra is formed. The cyclization reaction of the ester of formula VI is preferably effected at a temperature in the range of +30° to 150° C. It will be observed that in this series of reactions, it is not necessary that one of $R^1$, $R^2$ and $R^3$ be an alkyl group. In fact, all of the moieties $R^1$, $R^2$ and $R^3$ can be hydrogen, all of the moieties $R^1$, $R^2$ and $R^3$ can be alkyl or some of the moieties $R^1$, $R^2$ and $R^3$ can be alkyl while others are hydrogen.

Compounds of formula (Ib) are prepared from the corresponding halogenated lactone whose formula is

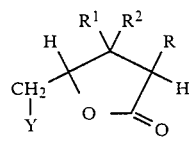
IX wherein $R^1$, $R^2$ and $R^3$ are hydrogen or the same or different alkyl group of 1 to 10 carbon and Y is Cl or Br. These compounds can be prepared in the manner described above from a pentene carboxylic acid whose formula is

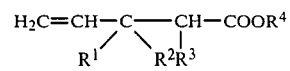

wherein each $R^1$, $R^2$ and $R^3$ is independently hydrogen or $C_1$ to $C_{10}$ alkyl group.

In such formula $R^4$ is a $C_1$ to $C_4$ alkyl group, hydrogen or an alkali metal or an alkaline earth metal. The compound in turn is reacted with chlorine or bromine under the conditions set forth above to saturate the ring and form the corresponding dihalo propane dicarboxylic acid (ester). The halogenation forms a compound of the formula

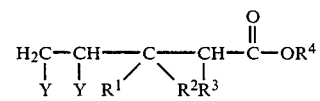

wherein each Y moiety is independently chlorine or bromine. The same when heated at 150° to 200° C. forms the corresponding lactone:

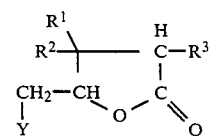

It will be observed that each moiety $R^1$, $R^2$ and $R^3$ is independently hydrogen or $C_1$-$C_{10}$ alkyl.

When the lactone is reacted with a base it forms a corresponding epoxide also as set forth above with $R^1$, $R^2$ and $R^3$ being equal to hydrogen, preferably. The corresponding epoxide of the formula

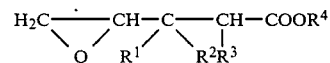

is in turn reacted with an acid to effect preparation of a compound of the formula Ib

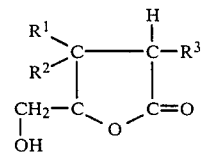
Ib which is the starting compound for a process in accordance with the invention.

The reaction to prepare a compound of formula V and VI as well as the use of the latter compound for the preparation of an acetal of 2,2-dialkyl-3-formyl cyclopropane carboxylic acid ester of formula (VIII) above, follows the reaction scheme set forth below

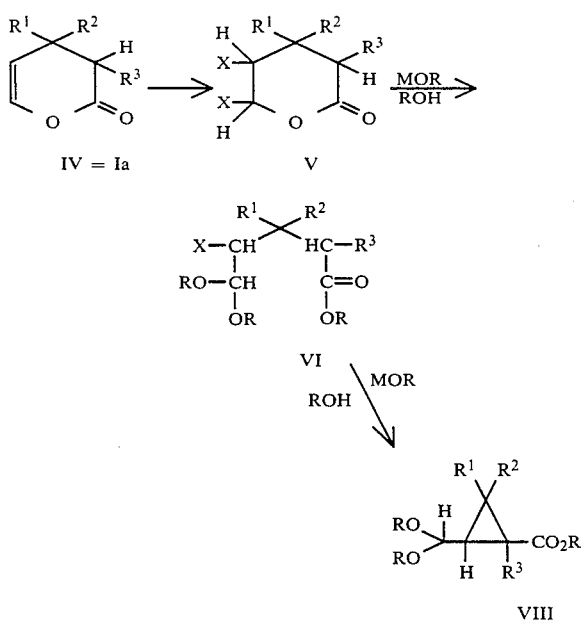

The halogen addition to the dihydro pyrone compound of formula IV is conducted in an inert organic reaction medium employing an inert organic solvent preferably a liquid chlorinated hydrocarbon such as carbon tetrachloride. The halogen, chlorine or bromine, is dosed into the reaction mixture at a temperature of between −50° and +40° C. Preferably, the temperature is between −10° and +40° C. At the end of the reaction the solvent is eliminated by distillation at reduced pressure such as vacuum inducted by an aspirator using for example flowing water. In this matter the dihalo lactone of formula V can be obtained and with or without further purification it can be employed to form the acetal by reaction of an alkali metal or alkaline earth metal alcoholate in the presence of an alkanol.

The dihalo lactone is thereafter reacted with 0.8 to 1.2 fold stoichiometric amount of an alcoholate of formula VI in the presence of a superstoichiometric amount of an alkanol of formula (VII) above, these being alcoholates and alcohols respectively whose alkyl group contains 1 to 4 carbon atoms. Preferably, the alcoholate is an alkali metal alcoholate especially sodium alcoholate e.g. sodium methylate. The reaction is conducted preferably at a temperature between −10° and +60° C. Preferably the temperature is between −10° and +40° C. The alcohol is employed in a stoichiometric excess preferably between 2 and 200 molar excess. The resultant acetal can be worked up by extraction with water and distillation of the raw product. If the reaction mixture contains no excess alcoholate, the same can be distilled directly after the reaction.

Cyclization to form the cyclopropane carboxylic acid ester of formula (VIII) above is effected with the help of the stoichiometric amount of a metal alcoholate of formula VIIb. The reaction is performed in a reaction mixture preferably containing an organic solvent. For this purpose, an alcohol of the alcoholate can be employed, preferably. In addition, there can be employed as other inert solvents compositions such as diethyl ether. The cyclization is effected at a temperature between +30° and 150° C.

The cyclic compounds of formula (VIII) are obtained in a cis, trans-mixture.

The cyclic compounds of formula (VIII) can be prepared with or without isolation of the intermediate acetal VI. In this case 1.8 to 2.2 fold of stoichiometric amount of metal alcoholate of formula (V) is employed in the presence of a stoichiometric excess of alkanol of formula (VIIa), preferably employed in a 2 to 200 molar excess. The temperature will range from between −10° to +60° C. at the commencement of the reaction and temperatures of up to +30° to +150° C. will develop during the reaction. It is, however, also possible that the reaction is performed without isolation of an intermediate product and the reaction is carried out at a temperature in the range of +30° to +60° C.

The compounds of the formula (VIII) can be used to prepare the free aldehyde. The free aldehyde is an important intermediate in preparation of insecticides of the Pyrethroid class. Such preparation is described e.g. in "Nature", London (1913), 244, 456.

In order to more fully illustrate the invention in the manner of practicing the same, the following Examples are presented.

EXAMPLE 1

8.0 g dihydro-5-hydroxymethyl-(3H)-furanone are trickled at a temperature of 300° C. over a period of 80 minutes through a heatable quartz tube 30 cm long and 2.2 cm in diameter which is filled with montmorillonite-spheres, and are collected in a cooled receiver. 5.9 g 3,4-dihydropyrone are obtained.

$^1$H-NMR spectrum (30 MHz): ppm=2.0–3.0 (m, 4H), 5.40 (m, 1H), 6.65 (m, 1H).

EXAMPLE 2

An electrically heated thermolysis tube 1.5 cm long and 1.24 cm in diameter is packed with 1.0 g of (spherical catalyst. 2 g of dihydro-5-hydroxymethyl-4,4dimethyl-2(3H)-furanone is dripped over the catalyst packing under $N_2$. The reaction mixture is captured in a cooled device and analyzed gas-chromotographically. Table 1 shows the results.

TABLE I

| Catalyst spherical | Material recovered subsequent to thermolysis | Temperature | Yield of 4,4-di-methyl-3,4-dihydro-alpha-pyrone (%) in terms of starting product |
|---|---|---|---|
| None (tube charged with quartz spheres) | 96% | 330° C. | 0 |
| Zeolite | | | |
| Mordenite Na form | 96% | 330° C. | 48 |
| Mordenite H form | 88% | 330° C. | 76 |
| Synthetic zeolites | | | |
| Type A | 91% | 330° C. | 30 |
| Type Z | 85% | 330° C. | 70 |
| Type A in Ca form | 95% | 330° C. | 10 |
| Montmorillonite | | | |
| KA 2 | 93% | 330° C. | 32 |
| K 306 | 90% | 330° C. | 50 |
| $SiO_2$ | 90% | 330° C. | 51 |
| $Al_2O_3$ | 87% | 330° C. | 69 |
| $Al_2O_3/SiO_2 + H_3PO_4$ | 92% | 330° C. | |
| Clay | 80% | 360° C. | 62 |

TABLE II

| Catalyst (powder form) | Material recovered subsequent to thermolysis | Temperature | Yield of 4,4-dimethyl-3,4-dihydro-alpha-pyrone (%) in terms of starting product |
| --- | --- | --- | --- |
| Zeolite | appr. 90% | 350° C. | 28 |
| Al$_2$O$_3$ | appr. 90% | 350° C. | 17 |
| ZrO$_2$ | 90% | 350° C. | 15 |
| V$_2$O$_5$ | 90% | 350° C. | 37 |
| ThO$_2$ on carrier | 85% | 350° C. | 28 |
| TiO$_2$ on carrier | 90% | 350° C. | 18 |
| Montmorillonite | 90% | 330° C. | 24 |

EXAMPLE 3

Dihydro-5Ohydroxymethyl-4,4-dimethyl-2(3H)-furanone was placed with a catalyst and/or solvent in a stirring flask and heated. The resulting distillation products were immediately withdrawn by distillation (see Table III).

TABLE III

| Catalyst | Solvent | Temperature | Yield of 4,4-dimethyl-3,4-dihydropyrone (in terms of starting product) |
| --- | --- | --- | --- |
| Al$_2$O$_3$ spheres | — | 330° C. | 26% |
| SiO$_2$ spheres | — | 330° C. | 29% |
| Zeolite (powder) | — | 330° C. | 28% |
| Zeolite | TCP* | 330° C. | 52% |
| H$_2$SO$_4$ Polyphosphoric acid | Decalin | 200° C. | 10% |
| P$_2$O$_5$ | | 320° C. | 37% |
| p-Toluene sulfonic acid | — | 250° C. | 15% |
| K$_2$HPO$_4$ | | 350° C. | 10% |
| KHSO$_4$ | | 350° C. | 30% |
| None | TCP* | 330° C. | 8% |
| None | None | 350° C. | 0% |

*TCP = Tricresylphosphate

As can be seen from the data above, it is critical in carrying out the process of the invention to have co-present a catalyst such as montmorillonite. If no catalyst is present, the yield of 4,4-di-methyl-3,5-di-hydro-alpha-pyrone in terms of the starting product is virtually nil. See especially the control of Table I and the last entry of Table III, supra. It is only by the use of the various catalysts of the process that significant amounts of 4,4-dimethyl-3,4-dihydro-alpha-pyrone are realized.

EXAMPLE 4

2 g dihydro-4-4,-dimethyl-5-hydroxymethyl-(3H)-furanone is dissolved in 20 ml toluene and this mixture is trickled under nitrogen, at a temperature of 300° C., over a period of 80 minutes through a heatable quartz tube 30 cm long and 2.2 cm in diameter which is filled with quartz shperes, and is collected in a cooled receiver. The toluene is eliminated at normal pressure by fractional distillation. The residue is distilled at 12 mm. 0.5 g 3,4-dihydro-4,4-dimethyl-α-pyrone (boiling point at 12 mm, 60° to 62° C.) is obtained. In addition, 1.3 g of starting product is recovered.

MH-NMR spectrum (100 MHz, CCl$_4$): δppm=1.12 (s, 6H); 2.40 (bs, 2H); 5.11 (d, 1H); 6.37 (d, 1H).

EXAMPLE 5

12.7 g 3,3-dimethylpentene-4-carboxylic acid methylester is dissolved in 18.9 ml carbon tetrachloride, and 14.3 g bromine in 44.9 ml carbon tetrachloride is added dropwise to this mixture at from 10° to 20° C. After elimination of the solvent in vacuum, 3,3-dimethyl-4,5-dibromopentane carboxylic acid methyl ester is obtained in a nearly quantitative yield.

NMR spectrum (30 MHz, CCl$_4$): δ=1.1 (s, 3H); 1.3 (s, 3H); 2.4 (s, 2H); 2.7 (s, 3H); 3.3 to 4.7 (m, 3H).

EXAMPLE 6

20.0 g 3,3-dimethyl-4,5-dibromopentane carboxylic acid methylester is refluxed in a fractional distillation apparatus for 30 minutes at a pressure of 0.8 mm and then fractionally distilled. At 95° to 96° C., 11.3 g dihydro-4,4-dimethyl-5-bromomethyl-(3H)-furanone distills over.

NMR spectrum (100 MHz, CCl$_4$): δ=1.10 (s, 3H); 1.26 (s, 3H); 2.41 (m, 2H); 3.55 (m, 2H); 4.37 (m, 1H).

EXAMPLE 7

43.7 g dihydro-4,4-dimethyl-5-bromomethyl-(3H)-furanone is dissolved in 166 ml methanol, and after the addition of 11.4 g sodium methylate this mixture is refluxed for 5 hours. The methanol is eliminated in vacuum and the residue is dissolved in water. The aqueous solution is extracted with ether and the organic phase is dried through a molecular sieve and fractionally distilled. At a pressure of 13 mm and a temperature of 86° to 88° C., 29.5 g 4,5-epoxy-3,3-dimethylpentane carboxylic acid methyl ester distills over.

$^1$H-NMR spectrum (100 MHz, CCl$_4$(: δ=0.95 (s, 3H); 0.98 (s, 3H); 2.22 (m, 2H); 2.52 (m, 2H); 2,77 (m, 1H); 360 (m, 3H).

EXAMPLE 8

21.1 g 4,5-epoxy-3,3-dimethylpentane carboxylic acid methyl ester is dissolved in 50 ml CCl$_4$ and the mixture is shaken for 5 hours with 12 ml 2N H$_2$SO$_4$. The organic phase is then separated and the aqueous phase extracted with ether, and the combined organic phases are dried by the use of a molecular sieve. After elimination of the organic solvent, there remains a crystalline residue (17.6 g) which is identified as dihydro-4,4-dimethyl-5-hydroxymethyl-(3H)-furanone. (Melting point, 40° to 42° C.).

$^1$H-NMR spectrum (100 MHz, CDCl$_3$): δ=1.08 (s, 3H); 1.17 (s, 3H); 2.37 (m, 2H); 3.77 (m, 2H); 4.15 (m, 1H); 3.80 (bs, 1H).

EXAMPLE 9

10.0 g 4,5-dihydro-5-bromomethyl-(3H)-furanone are refluxed with 3.0 g sodium methylate in 37 ml methanol for 5 hours. The solvent is eliminated in vacuum and the residue is dissolved in 20 ml H$_2$O and then extracted with ether. The ethereal phase is dried through a molecular sieve and the ether eliminated in vacuum. The residue is distilled at 20 mm. 6.4 g 4,5-epoxypentane carboxylic acid methyl ester (boiling point at 20 mm, 85° C.) is obtained.

EXAMPLE 10

6.0 g 4,5-epoxypentane carboxylic acid methyl ester is shaken in a mixture of 10 ml ether and 10 ml 2n HCl for 1 hour. The ether is then separated and the aqueous phase perforated with ether. From the combined dried ethereal phases 3.7 g dihydro-5-hydroxymethyl-(3H)-furanone is obtained after removal of the ether in vacuum.

EXAMPLE 11

17.6 g 4,4-dimethyl-3,4-dihydro-α-pyrone are dissolved in 45.0 g CCl$_4$, and 22.3 g bromine in 59 g CCl$_4$, dissolved at 5° to 10° C., is added dropwise to this mixture under stirring. After the dropping in the solvent is removed in water-jet vacuum. 39.5 g crystalline 4,4-dimethyl-5,6-dibromo-δ-valerolactone are obtained. (Melting point 85°–87° C. from CCl$_4$).

$^1$H-NMR spectrum (100 MHZ, CCl$_4$): $\delta_{ppm}$=1.16 (s, 3H), 1.24 l (s, 3H), 2.70 (m, 2H); centers at 4.32 and 4.41 (m, 1H); centers at 6.46–6.61 (m, 1H).

EXAMPLE 12

9.5 g 4,4-dimethyl-5,6-dibromo-δ-valerolactone are dissolved in 5.0 g methanol and 1.67 g Na-methylate, dissolved in 11.0 g methanol, are added dropwise for 2 hours under stirring at 20° C. to 30° C. Then the reaction mixture is poured into 50 ml H$_2$O and the water extracted with methylene chloride. After drying of the organic phase through a molecular sieve and removal of the solvent in water-jet vacuum 7.8 g 5,5-dimethoxy-4-bromo-3,3-dimethylpentanecarboxylic acid methyl ester are obtained.

$^1$H-NMR spectrum (30 MHZ, CCl$_4$): $\delta_{ppm}$=1.20 (s, 6H); 2.53 (s, 2H); 3.45 (s, 6H); 4.48 (s, 2H).

EXAMPLE 13

6.2 g 5,5-dimethoxy-4-bromo-3,3-dimethylpentane carboxylic acid methyl ester are dissolved in 3.3 g methanol and a solution from 1.3 g Na-methylate and 8.2 g methanol is added dropwise to this mixture. Then the mixture is stirred for 15 hours at 50° C. Then the reaction mixture is dissolved in water, extracted with diethylether and the organic phase is dried. After removal of the ether in water-jet vacuum the residue is distilled. 3.55 g cis, trans-2,2-dimethyl-3-formyl-(dimethylacetale)-cyclopropane carboxylic acid methyl ester are obtained.

EXAMPLE 14

0.5 g 4,4-dimethyl-3,4-dihydro-1-pyrone are dissolved in 4.5 g tetrachloromethane and 0.3 g gaseous chlorine is introduced into this mixture at 10° C. After removal of the solvent in water-jet vacuum 0.7 g cis, trans-4,4-dimethyl-5,6-dichloro-1-valerolactone is obtained.

$^1$H-NMR spectrum (30 MHZ, CCl$_4$): $\delta_{ppm}$: 1.25 (bs, 6H); 2.70 (bs, 2H); 4.15; 4.20 (2d, 1H); 6.15–6.45 (2d, 1H).

EXAMPLE 15

166 g 4,4-dimethyl-5,6-dichlorovalerolactone are dissolved in 124 g methanol at room temperature and a methanolic sodium-methylate solution (48 g NaOCH$_3$ in 247 g methanol) is added to this solution dropwise. The mixture is then stirred for 1 hour at room temperature. The methanol is removed in water-jet vacuum and the residue is distilled in high vacuum in small portions. 187.8 g 5,5-dimethoxy-4-chloro-3,3-dimethylpentane carboxylic acid methyl ester are obtained (boiling point 0.1 mm Hg 117°–119° C.).

$^1$H-NMR spectrum (80 MHZ, CDCl$_3$): $\delta_{ppm}$=1.19 (s, 6H); 2.51 (m, 2H); 3,43 (s, 3H); 3.44 (s, 3 H); 3.66 (s, 3H); 4, 24 (d, 1H); 4.50 (d, 1H).

EXAMPLE 16

8.0 g 5,5-dimethoxy-4-chloro-3,3-dimethylpentane carboxylic acid methyl ester are stirred in 30 ml diethyleneglycol-dimethylether with 2.2 g NaOCH$_3$ for 5 hours at 110° C. The sodium chloride thus obtained is filtered off, washed with diethyl ether and the organic phases are combined. After removal of the diethyl ether in vacuum the diethylene glycol-ether is distilled off in water-jet vacuum and the residue is distilled in high vacuum. 5.2 g 2,2-dimethyl-3-formyl-(dimethylacetale)-cyclopropane carboxylic acid methyl ester are obtained.

EXAMPLE 17

17.6 g 4,4-dimethyl-3,4-dihydro-α-pyrone is dissolved in 45 g CCl$_4$, and to this mixture 22.3 g bromine in 59 g CCl$_4$, dissolved at 5° to 10° C., is added dropwise with stirring. Following this dropwise addition, the solvent is eliminated in a water-jet vacuum. 39.5 g of crystalline 4,4-dimethyl-5,6-dibromo-δ-valerolactone is so obtained. (Melting point, 85° to 87° C. from CCl$_4$) $^1$H NMR spectrum (100 MHz, CCl$_4$): $\delta_{ppm}$=1.16 (s, 3H), 1.24 l (s, 3H), 2.70 (m, 2H); centers at 4.32 and 4.41 (m, 1H); centers at 6.56–6.51 (m, 1H).

EXAMPLE 18

9.5 g 4,4-dimethyl-5,6-dibromo-δ-valerolactone is dissolved in 5 g methanol, and to this mixture 1.67 g sodium methylate, dissolved in 11 g methanol, is added dropwise with stirring over a period of 2 hours at 20° to 30° C. The reaction mixture is then poured into 50 ml H$_2$O, which is then extracted with methylene chloride. After drying of the organic phase by the use of a molecular sieve and elimination of the solvent in a water-jet vacuum, 7.8 g 5,5-dimethoxy-4-bromo-3,3-di-methylpentane carboxylic acid methyl ester is obtained.

$^1$H NMR spectrum (30 MHz, CCl$_4$): $\delta_{ppm}$=1.20 (s. 6H); 2.53 (s, 2H); 3.45 (s, 6H), 4.48 (s, 2H).

EXAMPLE 19

6.2 g 5,5-dimethoxy-4-bromo-3,3-dimethylpentane carboxylic acid methyl ester is dissolved in 3.3 g methanol and to this mixture ester is dissolved in 3.3 g methanol and to this mixture a solution of 1.3 g sodium methylate and 8.2 g methanol is added dropwise. This mixture is stirred for 15 hours at 50° C. The reaction mixture is then dumped into water and extracted with diethyl ether, and the organic phase is dried. After elimination of the ether in a water-jet vacuum, the residue is distilled: 3.55 g cis, trans-2,2-di-methyl-3-formyl-(dimethylacetal)-cyclopropane carboxylic acid methyl ester is so obtained.

EXAMPLE 20

0.5 g 4,4-dimethyl-3,4-dihydro-α-pyrone is dissolved in 4.5 g tetrachloromethane, and into this mixture 0.3 g gaseous chlorine is introduced at 10° C. After elimination of the solvent in a water-jet vacuum, 0.7 g cis, trans-4,4-dimethyl-5,6-dichloro-δ-valerolactone is obtained.

$^1$H NMR spectrum (30 MHz, CCl$_4$): $\delta_{ppm}$: 1.25 (bs, 6H); 2.70 (bs, 2H); 4.15; 4.20 (2d, 1H); 6.15–6.45 (2d, 1H).

EXAMPLE 21

166 g 4,4-dimethyl-5,6-dichlorovalerolactone is dissolved in 124 g methanol at room temperature, and to this solution a methanol solution of sodium methylate (48 g NaOCH$_3$ in 247 g methanol) is added dropwise. The mixture then is stirred for another hour at room temperature. The methanol is eliminated in a water-jet vacuum, and the residue is distilled in small portions in a high vacuum. 187.8 g 5,5-di-methoxy-4-chloro-3,3-dimethylpentane carboxylic acid methyl ester is so obtained. (Boiling point 0.1 mm Hg: 117°–119° C.

$^1$H NMR spectrum (80 MHz, CDCl$_3$): $\delta_{ppm}$=1.19 (s, 6H); 2.51 (m, 2H); 3.43 (s, 3H); 3.44 (s, 3H); 3.66 (s, 3H); 4.24 (d, 1H); 4.50 (d, 1H).

EXAMPLE 22

8 g 5.5-dimethoxy-4-chloro-3,3-dimethylpentane carboxylic acid methyl ester is stirred in 30 ml diethylene glycol dimethyl ester is stirred in 30 ml diethylene glycol dimethyl ether with 2.2 g NaOCH$_3$ for 5 hours at 110° C. The sodium chloride formed is filtered off and washed with diethyl ether and the organic phases are combined. After elimination of the diethyl ether in a vacuum, the diethylene glycol ether is distilled off in a water-jet vacuum and the residue is distilled in a high vacuum. 5.2 g 2,2-dimethyl-3-formyl-(dimethylacetal)-cyclopropane carboxylic acid methyl ester is so obtained.

What is claimed is:

1. A process for the preparation of a lactone of the formula

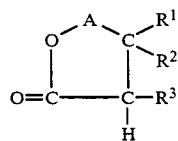

wherein A is a —CH=CH-moiety, R$^1$, R$^2$, and R$^3$ are hydrogen or C$_1$ to C$_{10}$ alkyl which comprises heating a lactone of the formula

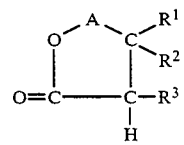

wherein A is a

group and R$^1$, R$^2$, and R$^3$ have the meaning given above at a temperature ranging from 200° to 500° C.

2. A process according to claim 1, wherein the heating is performed in the presence of a catalyst.

3. A process according to claim 2, wherein said catalyst is an oxide of aluminum, silicon, chromium, iron, gallium, tungsten, molybdenum, thorium, zinc, titanium, zirconium, nickel, manganese, vanadium or a rare earth metal or a mixed oxide thereof.

4. A process according to claim 2, wherein said catalyst is an alumino silicate.

5. A process according to claim 4, wherein said alumino silicate is a crystalline alumino silicate zeolite.

6. A process according to claim 4, wherein said alumino silicate is a non-zeolytic alumino silicate.

7. A process according to claim 4, wherein said alumino silicate is a clay.

8. A process according to claim 4, wherein said alumino silicate is montmorillonite.

9. A process according to claim 2, wherein the catalyst is a sheet silicate.

10. A process according to claim 2, wherein said catalyst is an alkali or alkaline earth metal salt of a sulfur acid or phosphorus acid.

11. A process according to claim 2, wherein said catalyst is a Bronsted or Lewis acid.

12. A process according to claim 2, wherein said catalyst is an anhydride of an organic or inorganic acid.

13. A process according to claim 2, wherein said catalyst is an ester of an inorganic acid.

14. A process according to claim 12, wherein said catalyst is P$_2$O$_5$.

15. A process according to claim 12, wherein said catalyst is a supported catalyst.

16. A process according to claim 1, wherein the process is carried out employing a catalyst in an amount of less than 100 weight percent, based upon the weight of the reaction mixture.

17. A process according to claim 1, wherein the process is carried out in the presence of a solvent.

* * * * *